US012144590B1

(12) United States Patent
Smith et al.

(10) Patent No.: US 12,144,590 B1
(45) Date of Patent: Nov. 19, 2024

(54) DEVICES AND METHODS FOR MEASURING JUGULAR VENOUS PRESSURE (71) Applicant: JRAS Medical Inc., St. John's (CA)

(72) Inventors: Andrew J. Smith, St. John's (CA);
Andrew M. L. Smith, St. John's (CA);
Jason Roberts, St. John's (CA)

(73) Assignee: JRAS MEDICAL, INC., St. John's (CA)

( * ) Notice: Subject to any disclaimer, the term of this patent is extended or adjusted under 35 U.S.C. 154(b) by 462 days.

(21) Appl. No.: 17/179,974

(22) Filed: Feb. 19, 2021

Related U.S. Application Data

(60) Provisional application No. 62/978,555, filed on Feb. 19, 2020.

(51) Int. Cl.
*A61B 5/0205* (2006.01)
*A61B 5/00* (2006.01)
(Continued)

(52) U.S. Cl.
CPC ............ *A61B 5/0205* (2013.01); *A61B 5/021* (2013.01); *A61B 5/14551* (2013.01);
(Continued)

(58) Field of Classification Search
CPC ..... A61B 5/0205; A61B 5/021; A61B 5/6822; A61B 5/6823; A61B 5/0077; A61B 2562/0247
See application file for complete search history.

(56) References Cited

U.S. PATENT DOCUMENTS

| 7,769,420 B2 | 8/2010 | Silver et al. |
| 11,234,643 B2 | 2/2022 | Nahmias et al. |

(Continued)

FOREIGN PATENT DOCUMENTS

| CA | 3038097 A1 | 9/2020 |
| CN | 205597908 U | 9/2016 |

(Continued)

OTHER PUBLICATIONS

Abnousi, F. et al., A novel noninvasive method for remote heart failure monitoring: the EuleriAn video Magnification apPLications In heart Failure and studY (AMPLIFY), npj Dig. Med. 80, 1-6 (2019).

(Continued)

*Primary Examiner* — Tammie K Marlen
(74) *Attorney, Agent, or Firm* — HILL & SCHUMACHER (57) ABSTRACT

Device for measuring jugular venous pressure of a human patient, comprising: (1) A body including a base configured to rest on the patient and align with at least one of the patient's manubrium, sternum and sternal angle and a light emitter assembly configured to project a pattern of light onto the neck of the patient proximate to the patient's jugular vein. (2) Two side arms extending from the body, each side arm being configured to rest on at least one of the patient's upper chest and clavicle. (3) At least one camera associated with one of the side arms, the at least one camera positioned and oriented to capture images of the patient's neck with the pattern of light projected thereon. Methods are also disclosed.

24 Claims, 4 Drawing Sheets

(51) Int. Cl.
 *A61B 5/021* (2006.01)
 *A61B 5/1455* (2006.01)
 *G06T 7/70* (2017.01)

(52) U.S. Cl.
 CPC .......... *A61B 5/6822* (2013.01); *A61B 5/6823* (2013.01); *G06T 7/70* (2017.01); *A61B 5/0077* (2013.01); *A61B 2562/0219* (2013.01); *A61B 2562/0247* (2013.01)

(56) References Cited

U.S. PATENT DOCUMENTS

| | | |
|---|---|---|
| 2006/0224053 A1 | 10/2006 | Black et al. |
| 2007/0093702 A1 | 4/2007 | Yu et al. |
| 2008/0294070 A1 | 11/2008 | Knori |
| 2010/0094141 A1 | 4/2010 | Puswella |
| 2013/0150735 A1 | 6/2013 | Cheng |
| 2014/0330335 A1* | 11/2014 | Errico .................. A61B 5/6898 607/45 |
| 2017/0027457 A1 | 2/2017 | Wagle et al. |
| 2017/0164904 A1 | 6/2017 | Kirenko |
| 2017/0172434 A1 | 6/2017 | Amelard et al. |
| 2017/0296119 A1 | 10/2017 | Debusschere |
| 2018/0177464 A1 | 6/2018 | Debusschere et al. |
| 2020/0008684 A1 | 1/2020 | Feinberg |
| 2020/0121262 A1 | 4/2020 | De Haan |
| 2020/0383578 A1 | 12/2020 | Smith et al. |
| 2022/0039665 A1 | 2/2022 | Smith et al. |

FOREIGN PATENT DOCUMENTS

| | | |
|---|---|---|
| CN | 206556660 U | 10/2017 |
| EP | 1534386 A1 | 6/2005 |
| GB | 2408935 A | 6/2005 |
| WO | 03101534 A1 | 12/2003 |
| WO | 2010009141 A1 | 1/2010 |
| WO | 2018161159 A1 | 9/2018 |
| WO | 2020051676 A1 | 3/2020 |

OTHER PUBLICATIONS

Amelard, R. et al., Ph.D. Thesis, University of Waterloo, 2017, "Widefield Computational Biophotonic Imaging for Spatiotemporal Cardiovascular Hemodynamic Monitoring", Thesis/Dissertation, 123 pages.

Garcia-López, I. et al., "Extracting the Jugular Venous Pulse from Anterior Neck Contact Photoplethysmography", Nat. Sci. Rep. 10, 3466 (2020). 12 pages.

Lam Po Tang, E. J. et al., "Non-contact Quantification of Jugular Venous Pulse Waveforms from Skin Displacements", Nat. Sci. Rep. 8, 17236 (2018), 12 pages.

Amelard R, Hughson RL, Greaves DK, Pfisterer KJ, Leung J, Clausi DA, Wong A., "Non-contact hemodynamic imaging reveals the jugular venous pulse waveform", Sci Rep. Jan. 9, 2017;7:40150. doi: 10.1038/srep40150. PMID: 28065933; Pmcid: PMC5220303, 10 pages.

International Search Report PCT/CA2022/051177 dated Nov. 18, 2022, 3 pages.

* cited by examiner

DEVICES AND METHODS FOR MEASURING JUGULAR VENOUS PRESSURE

CROSS-REFERENCE

The present application claims priority to U.S. Provisional Patent Application No. 62/978,555, filed Feb. 19, 2020, entitled "Devices and Methods for Measuring Jugular Venous Pressure". The present application is related to International Patent Application Publication No. WO 2018/161159 A1, published Sep. 13, 2018, entitled "Jugular Venous Pressure Measurement Devices". The present application is also related to U.S. Provisional Patent Application 62/730,416, filed Sep. 12, 2018, entitled "Jugular Venous Pressure Measurement Devices". The present application is also related to U.S. Provisional Patent Application 62/857,717, filed Jun. 5, 2019, entitled "Systems and Methods for Remote Assessment of Jugular Venous Pressure". Each of the foregoing applications is incorporated by reference herein in its entirety for all purposes.

FIELD

The present technology relates to devices and methods for measuring the jugular venous pressure.

BACKGROUND

Remote patient monitoring systems for patients with congestive heart failure generally monitor heart rate, blood pressure, oxygen saturation, and other physiological signs in order to remotely monitor a patient's health status. This, in turn, enables healthcare providers to adjust medications, suggest lifestyle changes and advise the patient to visit their doctor, all with the goal of optimizing the patient's health while reducing preventable hospital admissions. Unfortunately, these signs and symptoms are indirect markers of volume status and have been shown to be poor predictors of which patients with congestive heart failure (CHF) will require readmission to hospital. The jugular venous pressure (JVP) is thought to be one of the better (direct) predictors of volume status for patients with CHF.

Patients initially diagnosed with CHF are routinely admitted to hospital for shortness of breath due to volume overload. They are started on medications including diuretics to remove this fluid. Once stabilized, patients are often discharged with a plan to be reassessed within 2-4 weeks for medication adjustment. Unfortunately, patients often need more frequent medication adjustment in order to prevent excess fluid from reaccumulating in the body.

Conventionally, assessment of the JVP involves determining the height of a column of blood in a neck vein (i.e., internal jugular vein) just below the skin. Typically, the patient is placed in a semi-recumbent position, in the range of 30°-60° to the horizontal, with the head slightly rotated away from the side being examined (10°-30° rotation). The clinician then examines the patient's neck to determine the height of the venous column demarked by the highest biphasic pulsation of the skin (as opposed to the monophasic pulsation of the adjacent carotid artery). The vertical height of the biphasic pulsation is measured relative to the patient's sternal angle. Unfortunately, assessment of the JVP has been noted to be frequently inaccurate, challenging to measure, and generally only measured properly in a clinical setting by those assessing JVP's on a regular basis. This is a major clinical issue as optimal management of CHF patients depends upon accurate detection of the biphasic pulsation and measurement of its height. Yet, currently patients are discharged from hospital without being able to have their JVP regularly reassessed outside of clinical setting.

There is therefore a need for a system and methods for extending JVP assessment outside of the clinical setting while also creating the opportunity to improve both the accuracy and reproducibility of the technique, over at least some conventional methods.

SUMMARY

It is an object of the present technology to ameliorate at least some of the inconveniences present in the prior art.

In one aspect, implementations of the present technology provide a device for measuring jugular venous pressure of a human patient, comprising: (i) a body (which may, in various implementations, be a central body or an off-center body), the body including: (a) a base, the base configured to rest on the patient and align with (i.e., with respect to) at least one of the patient's manubrium, sternum and sternal angle, and (b) a light emitter assembly configured to project a pattern of light onto the neck of the patient proximate to the patient's jugular vein. The device also comprises two side arms extending from the body. Each side arm is configured to rest on at least one of the patient's upper chest and clavicle. The device also comprises a camera associated with one of the side arms. The camera is positioned and oriented to capture images of the patient's neck with the pattern of light projected thereon. (In the context of the present specification, "images" includes a single image, multiple discrete images, video, and video streams.)

The present technology thus provides a single device which is repeatably and accurately positionable in the same location with respect to a patient's body over time. That location is appropriate to capture images (and particularly video streams) of the patient's neck, allowing for a JVP reading to be made with height measured relative to the sternal angle. The present technology allows multiple images (e.g., video streams) to be captured (and thus JVP readings to be made) over a period of time with the device placed in the same location on the patient. (Capturing a video stream (as opposed to a single image or even multiple images) is helpful is it allows one to ensure that the height of the blood in the jugular vein can be correctly determined over multiple cardiac cycles.) Further, the present technology also allows for the camera(s) to be (relatively) stable during the process of image capture (for example, as compared to a prior art technique such as trying to capture such images with a (handheld) smartphone or tablet). Finally, the present technology, by projecting a known pattern of light from a known fixed location in relation to the sternal angle of the patient, ensures that there is a known or mathematically calculatable relationship between the height of the blood in the jugular vein and the pattern of light, both of which are shown in the captured image(s). Thus, the present technology attempts to ensure that multiple JVP readings can be made in a non-clinical setting and that such readings are accurate, and reliably comparable one to another.

In some implementations, the device can be used by the patient remotely (i.e., outside of the clinical setting, e.g., in their home) without requiring a practitioner experienced in the field of JVP measurement to be present. Remote monitoring of the JVP promises to enable better titration of medication and reduce readmission rates.

To assist in the proper alignment of the device on the patient's body, the body of the device is provided with base which in some implementations acts an alignment tool. For example, in some implementations, the base (including additional attachments thereto) has a protrusion that fits into a patient's sternal notch (which is an anatomical landmark that is relatively easy for patients to find). By fitting this protrusion into the sternal notch, the base becomes properly aligned with respect to the sternum, sternal angle, and/or manubrium. Other possible anatomical landmarks that may be used in other implementations to position the device include the midline heads of the clavicle. (Such protrusions are not required, and in some implementations, the device can be properly aligned with respect to the sternum, sternal angle, and/or manubrium without any of these landmarks.).

The proper alignment of the device is, in many implementations, the base being centered over the sternum, sternal angle and/or manubrium, but this is not the case in all implementations. The proper alignment will depend on the particular construction and/or design of the device.

In some implementations, the base is configured to rest on at least one of the patient's manubrium, sternum and sternal angle. But this is not the case in all implementations of the present technology. In some implementations the device may be properly aligned with respect to the patient's body without the base being configured to rest on any of the patient's manubrium, sternum and sternal angle: the device may simply pass over sternum, sternal angle and/or manubrium in some implementations.

In some implementations, the base is a generic base of an appropriate size and shape for a particular patient range. In other implementations, the base is a specific base that has been particularly sized and shaped for a particular patient. In some implementations the base is removably attached to the device, allowing for different bases to be attached (at different times) to the same device. In other implementations, the base is non-removably attached to the device.

In some implementations, additional structures, e.g., adapters, covers, etc., can be fitted to or attached to the base to allow for a more particularized fit of the base (and the device) to the patient.

The device also comprises two side arms extending from the body. Each side arm is configured to rest on at least one of the patient's upper chest and clavicle (be it with or without clothing). In some implementations, each side arm is also configured to wrap partially around a side of the patient's neck, and in other implementations, fully. In some implementations, the side arms are separate structures from one another and are not portions of single unitary structure. In some of those implementations, the side arms may, when placed on a patient, connect to one another for a variety of purposes (e.g., stabilization of the device). (Such connection may be achieved through any number of conventional fasteners (e.g., mechanical connectors, magnets, etc.) In other such implementations, the side arms do not so connect with one another. In still other implementations, the side arms are portions of single unitary structure (e.g., a ring, a torus etc.)

Depending on the structure of any particular device, the side arms can serve one or more of a number of purposes, including: (a) helping to position the device in the correct position on the body of the patient, (b) helping to retain the device in the correct position on the body of the patient, (c) serving as a structure to receive, contain, mount, connect, etc. other functional structures of the device (e.g., a camera or multiple cameras). Furthermore, in different implementations, depending on the structure and functions of the side arms, the side arms may be of varying rigidity or flexibility, sufficient to carry out their intended purposes. Thus, in some implementations the side arms are relatively rigid. In other implementations the side arms are relatively flexible. As a non-limiting example, sufficient flexibility may enable the side arms to more appropriately fit the size and/or shape of a particular patient that using the device.

Furthermore, for example, in some implementations the side arms may be moveable and/or flexible allowing for the device to be correctly positioned on the patient (e.g., with the base on or over the patient's manubrium, sternum and/or sternal angle) with the side arms being away from the neck of the patient. Once the device is correctly positioned, the side arms can be repositioned to be proximate the neck of the patient, securing the device in place. In some implementations, the side arms may contain a spring-like mechanism clasping them around the neck. In other implementations, the side arms can loop-up over the upper trapezius stabilizing on them (almost like hooks). For example, in some such implementations, the side arms may have portions and/or components that bend over the shoulder and/or upper trapezius that are made of a soft flexible material such as silicone. These portions and/or components can be appropriately selected depending on the size of the patient. (In some such embodiments these portions or components can be designed to "spring" slightly behind the neck of the patient to assist in properly positioning the device and/or maintaining the device properly positioned (e.g., by stabilizing the device and preventing it from falling forward when on the patient). For example, as the patient places the device around their neck, such silicone components could brush along the sides of the patient's neck and spring back into place once the device is properly positioned.

Having the side arms be moveable and/or flexible can provide a variety of positions such that a camera disposed within a side arm can be positioned to be able to capture an image of the entire neck of the patient (if so desired). (This could also be accomplished via camera lenses, if so desired.) Another potential advantage of moveable/flexible side arms is that the device can likely then be used on a wider variety of body shapes/sizes (than would be the case with immoveable/inflexible side arms). In addition, in some implementations the side arms (and/or portions and/or components thereof) may be removeable from the device and replaceable with portions/components of a different size, shape, configuration, orientation, etc. Having a device of such a construction will also assists in rendering the device more customizable and compatible with a wider variety of body shapes/sizes. In some implementations the device can thus be tailored (as much as the device and its components allow) in a clinical setting and given to the patient for use outside of the clinical setting with the knowledge that the "tailoring" increases the probability that the device will be repeatably correctly positioned each time the device is used by the patient outside of the clinical setting.

Optionally, in some implementations, the rear portions of the side arms maybe tapered/flattened in a way such that they align with the contour of the back of the patient's neck. Thus, when the patient lies down on a wedge pillow (as described hereinbelow), the device does not materially move.

In some implementations, the device is structured to have the overall shape of a "collar" that is easily put on and taken off by the elderly and/or other laypeople (e.g., people who are frail, people who have tremors, people who have a limited range of motion above their head, etc.) In such implementations, the device is structured (and optionally tailored as described hereinabove) to allow such individuals to place the device accurately and repeatedly in the same position with respect to their bodies, without being fixedly attached there to their bodies. Thus, the goal in some such implementations is the design of the device takes greatly into consideration the relative ease for the patient to correctly position the device on their body time and time again.

The device also has a light emitter assembly configured to project a pattern of light onto the neck of the patient proximate to the patient's jugular vein. Depending on the implementation (and particularly the camera image sensor capture angle and the method by which camera images will be processed—discussed in further detail below), the light may be in the visible spectrum or may be IR or UV light (or some combination thereof). The light emitter(s) of the light emitter assembly(ies) may be any number of conventional light-emitting structures of appropriate size and shape. For example, such light emitters may be LED's, lasers, etc., and may have one or more optics (e.g., mirrors, prisms, lenses, etc.) to condition the light.

The light emitter assembly is structured and arranged so that the pattern of light is projected onto the same position of the patient's neck each time the device is correctly positioned and used. This will assist in ensuring that readings taken at different times are reliably comparable to one another. Thus, in different implementations (as is further discussed below) the light emitter assembly may be fixedly disposed on the device or may be moveably disposed on the device.

The pattern of the light projected onto the patient's neck by the light emitter may be any pattern sufficient to use as a reference by which the height of the blood in the patient's jugular vein may be determined. In the context of the present invention, no particular pattern is required as long the aforementioned functionality is present. As an example, a simple pattern consisting of a series of lines projected on or near the patient's jugular vein (with the lines being in a predetermined orientation each with respect to the others, running perpendicular to the vein) may suffice. In such an example, for example, the distance between the lines may be known or calculatable (either by a human or a machine).

It should be noted that, although in reality the jugular vein is slightly off-axis with respect to the neck, to simply things, an assumption can be made in measuring the JVP that the vein runs exactly in line with the neck.

The device also comprises a camera associated with one of the side arms. The camera may thus be disposed on the side arm, in the side arm, above the side arm, in front of the side arm, etc. In fact, no particular position of the camera with respect to the side arm is important as long as the image sensor of the camera is positioned and oriented in space with respect to the patient's neck such that the image sensor may capture images of the patient's neck having the pattern of light projected therein. This is not to say that the positioning of the camera (or cameras if there are more than one) is or must be random. There are many implementations, for example, one in which multiple cameras are used to enable stereovision, where the cameras are placed in particular positions (for example, with respect to the sternal angle).

In some implementations those images could be processable by a machine (e.g., computer) and/or interpretable by a human.

The camera and its connection to the side arm (whatever that may be) are structured and arranged so that images of the patient's neck may be captured by the camera from the same position and angle each time the device is correctly positioned and used. This will assist in ensuring that images taken at different times are reliably comparable to one another. In different implementations the camera may be fixedly disposed on the device or may be moveably disposed on the device.

In the present context, the camera being "fixedly disposed" is intended to mean that neither the camera body nor its image sensor's capture angle can be moved or changed without removing the camera from the device and physically repositioning or reorienting the camera (or both). For example, a device having a "fixedly disposed" disposed camera may be useful where the device is to be used by a patient outside of a clinical setting. In such a case, the device can be configured in a hospital with the camera (and its image sensor angle if such can be separately adjusted) being appropriately oriented and positioned so that images of the patient's neck (with the light pattern projected thereon) can be captured. And, once configured, the device can be given to the patient for use outside the hospital, and the images will always be captured from the same position and angle when the patient uses the device (assuming, of course, that the patient has correctly positioned the device on their body). Any means of fixation not incompatible with the functionality of the device is within the scope of the present technology. For example, in the clinical setting, there may be a number of different side arms of different sizes (and/or shapes) having cameras permanently affixed therein or thereon. The device may be constructed so that the physician only needs to pick the side arm having a camera that when attached to the central body provides the appropriate camera image sensor capture angle. Alternatively, the side arm and camera body may be constructed with a particular connector assembly that permits a practitioner to place the camera wherever they deem it appropriate to provide the appropriate camera image sensor capture angle. Once positioned the camera may be locked into place and may only be repositioned in the future by a practitioner in the clinical setting.

Alternatively, the camera may be movably disposed on the device. The camera being "moveably disposed" on the device is intended to mean that at least one of the camera body or its image sensor's capture angle can be moved or changed without removing the camera from the device.

In some implementations where the camera is moveably disposed, the camera may be disposed on or in the side arm via one or more gimbals operating in one or more axes that allow the camera (and its image sensor capture angle) to maintain predetermined orientation with respect to the patient's body. In such an example, a gimbal mounted camera may be appropriately weighed such that, merely by the effect of gravity, the camera image sensor capture angle remains appropriately positioned with respect to the neck of the patient, notwithstanding changes in the angle of the patient (for example) between measurements. (As a person skilled in the art would understand, a patient's JVP is measured when the patient is in a semi-recumbent position ranging between 30-60 degrees. So, the gimbal assembly and weights would be constructed with this design criterion in mind.)

Alternatively, in other implementations, an actuator may be connected to the gimbal (for example) to actively maintain the camera (and camera image sensor capture angle) in the appropriate position and orientation with respect to the patient's neck. No particular type actuator is required in the context of the present technology. Any actuator (e.g., one or more linear motors) not otherwise incompatible with the function of the device may be used. In most implementations, use of an actuator will allow the camera to be maintained in a wide variety of positions and/or orientations. This may be useful, for example, when the device has appropriate position sensor(s) (e.g., 3-axis accelerometer, gyroscope, etc.) and a determination can be made, when taking a JVP reading, of the variance in the position and orientation of the device from the previous time that a reading was made, and the position and/or orientation of the camera can be appropriately altered in consequence to account for the difference.

Additionally, or alternatively, information from the position sensor(s) may be used to adjust the position and/or orientation of the camera on the basis of the deviation of the then current position and/or orientation of the device from a standard (be it a permanent one or one which had been input into the device by the health care practitioner), such that the camera is positioned and/or oriented similarly each time a JVP reading is made notwithstanding differences in position or orientation of the device (or the patient).

Additionally, or alternatively, the camera itself may be equipped with an appropriate position sensor(s) to provide information as to then current position and/or orientation of the camera. This information (when present) can be used to assist in correctly positioning and/or orienting the camera.

In other implementations, the camera may be in electronic communication with a processor (of a computer system) capable of "machine vision" in combination with the camera, and such machine vision may be used to appropriately position the camera. ("Machine vision" in the present context refers to image-based computerized inspection and analysis in process control.)

As was stated to hereinabove, the light emitter assembly may also be fixedly disposed or moveably disposed. In the present context, the light emitter assembly being "fixedly disposed" is intended to mean that the position and orientation of the light emitter assembly cannot be changed without removing the light emitter assembly from the device and physically repositioning or reorienting the assembly. As was the case with the camera, the device having a "fixedly disposed" light assembly may be useful where the device is to be used by a patient outside of a clinical setting. In such a case, the device can be configured in a hospital with the light emitter assembly being appropriately oriented and positioned so that the light pattern is projected onto the patient's neck so as to be appropriately positioned with respect to the patient's jugular vein. Once configured, the device can be given to the patient for use outside of the hospital, and the light will always be projected onto the same portion of the patient's neck when the patient uses the device (assuming, of course, that the patient has correctly positioned the device on their body).

Any means of fixation not incompatible with the functionality of the device is within the scope of the present technology. For example, in the clinical setting, there may be a number of differently constructed (varying shape, size, light emission angle(s), etc.) light emitter assemblies. And, the device may be constructed so that the health care practitioner only needs to pick the light emitter assembly that is appropriate such that when attached to the device, the light emitter assembly projects the pattern onto the appropriate part of the patient's neck. In such an implementation, the light emitter assembly may not be repositionable without disassembly of the device.

Alternatively, the light emitter assembly may be constructed with a particular connector assembly that permits the practitioner to place the light emitter assembly in wherever orientation the practitioner deems appropriate to project the pattern onto the appropriate part of the patient's neck. Once oriented the light emitter assembly may be locked into place and may only be repositioned in the future by the physician in the clinical setting.

Alternatively, the light emitter assembly may be movably disposed on the device. The light emitter assembly being "moveably disposed" on the device is intended to mean that the light emitter assembly can be at least one of reoriented and repositioned without removing the light emitter assembly from the device.

In some implementations where the light emitter assembly is moveably disposed, the light emitter assembly may be disposed on or in the device via one or more gimbals operating in one or more axes that allow the light emitter assembly to maintain predetermined orientation with respect to gravity (vertical) and the patient's sternal angle. (In many implementations, it is the height above the patient's sternal angle that is important. In such an example, a gimbal mounted light emitter assembly may be appropriately weighed such that, merely by the effect of gravity, the light emitter assembly remains appropriately positioned with respect to the neck of the patient notwithstanding the angle of the patient. (As a person skilled in the art would understand, a patient's JVP is measured when the patient is in a semi-recumbent position ranging between 30-60 degrees. So, the gimbal assembly and weights would be constructed with this design criterion in mind.)

Alternatively, in other implementations, an actuator may be connected to (for example), the gimbal to actively maintain the light emitter assembly in the appropriate position and orientation with respect to gravity (vertical) and the patient's sternal angle. No particular type of actuator is required in the context of the present technology. Any actuator (e.g., one or more linear motors) not otherwise incompatible with the function of the device may be used. In most implementations, use of an actuator will allow the light emitter assembly to be maintained in a wide variety of positions and/or orientations. This may be useful, for example, when the device has appropriate position sensors and a determination can be made, when taking a JVP reading, of the variance in the position and orientation of the device from the previous time that a reading was made, and the position and/or orientation of the light emitter assembly can be appropriately altered in consequence to account for the difference.

In some implementations, the light emitter assembly (and, optionally the gimbals and/or the actuator, where present) may be enclosed in a fully transparent housing or partially transparent housing (e.g., one having appropriately placed "windows") to provide protection therefor while enabling light transmission. Such a housing may also facilitate cleaning of the device.

Alternatively, information from the device and/or camera position sensor(s) (if present) may be used to adjust the position and/or orientation of the light emitter assembly on the basis of the deviation of the then current position and/or orientation of the device from a standard (be it a permanent one or one which had been input into the device by the physician), such that the light emitter assembly is positioned and/or oriented similarly each time a JVP reading is made notwithstanding differences in position or orientation of the device (or the patient).

Additionally, or alternatively, the light emitter assembly itself may be equipped with an appropriate position sensor(s) to provide information as to then current position and/or orientation of the light emitter assembly. This information (when present) can be used to assist in correctly positioning and/or orienting the light emitter assembly.

As an example, information from position sensors can be used to determine if the device is on the patient and if the light assembly is oriented appropriately. Such information can also be processed and used to determine whether to project the pattern of light. For example, the light pattern can be projected throughout the entire time during which images are being captured by the camera or alternatively only during a portion of such time.

In other implementations, the light emitter assembly may be in electronic communication with a processor (of a computer system which itself is in communication with the camera) capable of "machine vision" in combination with the camera, and such machine vision may be used to appropriately position the light emitter assembly.

In some implementations, in a non-limiting example, a single reference image can be captured initially in a clinical setting (e.g., a hospital) with the light registered to the specific patient. Subsequent images of the neck captured outside of the clinical setting (e.g., in the home), along with the angle of inclination (from an accelerometer/gyroscope of the device) of the device (and hence the patient), can be used to calculate the vertical height of the column of blood in the jugular vein relative to the sternal angle or other anatomical feature using mathematics (e.g., trigonometry).

In a very simple implementation of the device, the light emitter assembly and the camera are both fixedly disposed on the device. The side arms of the device are rigid. Each of the light emitter assembly and the camera assembly are in electronic communication with a processor. The processor is in electronic communication with a battery, an on/off switch, a digital information storage medium, and a transceiver.

A method for measuring jugular venous pressure of a human patient, comprises: (1) positioning the device as described above on the patient, with the base of the device aligned with and resting on at least one of the patent's manubrium, sternum and sternal angle. (2) Wrapping the sides arms of the device around the patient's neck. (3) Causing the device to project the pattern of light onto the patient's neck proximate to the patient's jugular vein. (4) Causing the device to capture images of the patient's neck having the light pattern projected thereupon. (5) Causing the processing of the captured images to determine jugular venous pressure.

The device may be caused to project the pattern onto the patient's neck via any number of suitable means (with no particular means being critical to the present technology). For example, in some implementations, the device may have one or more physical switches which cause this to happen. In such implementations the project may be started simply by pressing a switch. The switch may be mechanical or electronic. Alternatively, or additionally, the device may be in electronic communication with a remote device (e.g., a smartphone) allowing for remote control. For example, in one implementation, the switch may be a virtual switch of an "app" of a smartphone with which the device is in electronic communication, and the device may be caused to project the pattern of light when the virtual switch is toggled.

The switch may implement a software-controlled process that controls more than the projection of the pattern. For example, that software process may also control the capturing of images of the light pattern, the storage of such images, the communication of such images to a remote device and/or the onboard processing of such images on the device. In implementations where the device includes one or more sensors and/or actuators, the software process may control such actuator(s) (at least in part) via information provided by such sensor(s). For example, the position and/or orientation of the light emitter assembly may be controlled to ensure the projection of the light pattern at the proper location.

The device may be caused to capture images of the patient's neck having the light pattern projected thereupon via similar means. For example, there may be a physical switch on the device which initiates the image capture process. Alternatively, or additionally, the image capture process may be initiated via a remote device (e.g., an app on a connected smartphone). Alternatively, or additionally, the image capture process may be automatically initiated via the software process that also controls the light pattern projection process. The process by which the image capture is controlled may simply capture a single image or may capture multiple images or video. The image capture process may be automatically periodically repeated.

The captured images may be stored in an information storage medium onboard the device. Alternatively, or additionally, the captured images may be transmitted to a remote device (e.g., a connected smartphone) for storage and/or processing. Once onboard the remote device, the images may be immediately processed to determine jugular venous pressure, or they may be stored for later processing. Alternatively, or additionally, the captured images may be transmitted to a second remote device (e.g., a remote server) for storage and/or processing.

Processing of the captured images to determine jugular venous pressure may be carried out by visual inspection of the captured images and/or via machine processing (e.g., artificial intelligence.). In some implementations, for example, to facilitate visual processing of the images a height scale (e.g., a virtual ruler) may be overlain on the captured images proximate to the patient's neck based on the detected position. For example, elements of the projected pattern of light would have known height relative to the sternal angel of the patient. The overlain height scale would enable visual inspection and measure of the vertical height of the JVP relative to the sternal angle.

Although not required to be used with the present technology, the present technology may be used in combination with the wedge pillows described in U.S. Provisional Patent Application 62/857,717, when measuring the JVP. Thus, for example, prior to taking the JVP, providing the patient with a plurality of wedge pillows, and the patient may be positioned at one of a plurality of recumbent angles by stacking the plurality of wedge pillows in one of a plurality of predetermined orientations. Having a standard protocol for JVP measurement using such a wedge pillow could be advantageous in some implementations. For example, the patient could first be asked to lie at 30-degrees on a wedge pillow, and a first set of JVP data could be recorded. The pillow could then be flipped on its end, and a second set of JVP data could be required. One advantage of such a protocol, could be that the JVP height could change between the positions and might optimally be visualized in one position or the other.

In the context of the present specification, the words "first", "second", "third", etc. have been used as adjectives only for the purpose of allowing for distinction between the nouns that they modify from one another, and not for the purpose of describing any particular relationship between those nouns. Thus, for example, it should be understood that, the use of the terms "first server" and "third server" is not intended to imply any particular order, type, chronology, hierarchy or ranking (for example) of/between the server, nor is their use (by itself) intended imply that any "second server" must necessarily exist in any given situation. Further, as is discussed herein in other contexts, reference to a "first" element and a "second" element does not preclude the two elements from being the same actual real-world element.

Implementations of the present technology each have at least one of the above-mentioned objects and/or aspects, but do not necessarily have all of them. It should be understood that some aspects of the present technology that have resulted from attempting to attain the above-mentioned object may not satisfy this object and/or may satisfy other objects not specifically recited herein.

Additional and/or alternative features, aspects and advantages of implementations of the present technology will become apparent from the following description, the accompanying drawings and the appended claims.

BRIEF DESCRIPTION OF THE DRAWINGS

For a better understanding of the present technology, as well as other aspects and further features thereof, reference is made to the following description which is to be used in conjunction with the accompanying drawings, where.

DETAILED DESCRIPTION

Referring to FIGS. 1 to 4, there is shown a JVP measurement device 100 in accordance with one implementation of the present technology. It is to be expressly understood that the JVP measurement device 100 is merely one implementation of the present technology. Thus, the description thereof that follows is intended to be only a description of an illustrative example of the present technology. This description is not intended to define the scope or set forth the bounds of the present technology. In some cases, what are believed to be helpful examples of modifications to the device 100 may also be set forth below. This is done merely as an aid to understanding, and, again, not to define the scope or set forth the bounds of the present technology. These modifications are not an exhaustive list, and, as a person skilled in the art would understand, other modifications are likely possible. Further, where this has not been done (i.e., where no examples of modifications have been set forth), it should not be interpreted that no modifications are possible and/or that what is described is the sole manner of implementing that element of the present technology. As a person skilled in the art would understand, this is likely not the case. In addition, it is to be understood that the device 100 may provide in certain aspects a simple implementation of the present technology, and that where such is the case they have been presented in this manner as an aid to understanding. As persons skilled in the art would understand, various implementations of the present technology may be of a greater complexity.

The JVP measurement device 100 comprises a body 110 configured to be received around a neck 300 of a patient, a base 120 configured to be placed on the manubrium 310 of the patient, a light emitter assembly portion 150 including a central body 152 for holding a light emitter 154. The light emitter 154 is configured to project a pattern of light 160 onto the neck 300 of the patient proximate the patient's jugular vein. The device 100 further includes a camera 130 housed in a camera housing 132 for capturing an image of the pattern of light 160 projected onto the neck 300 of the patient. (In other implementations, the device 100) could camera include multiple cameras, each with a known and fixed location with respect to the others to provide for stereovision, for example.)

Figure 1:
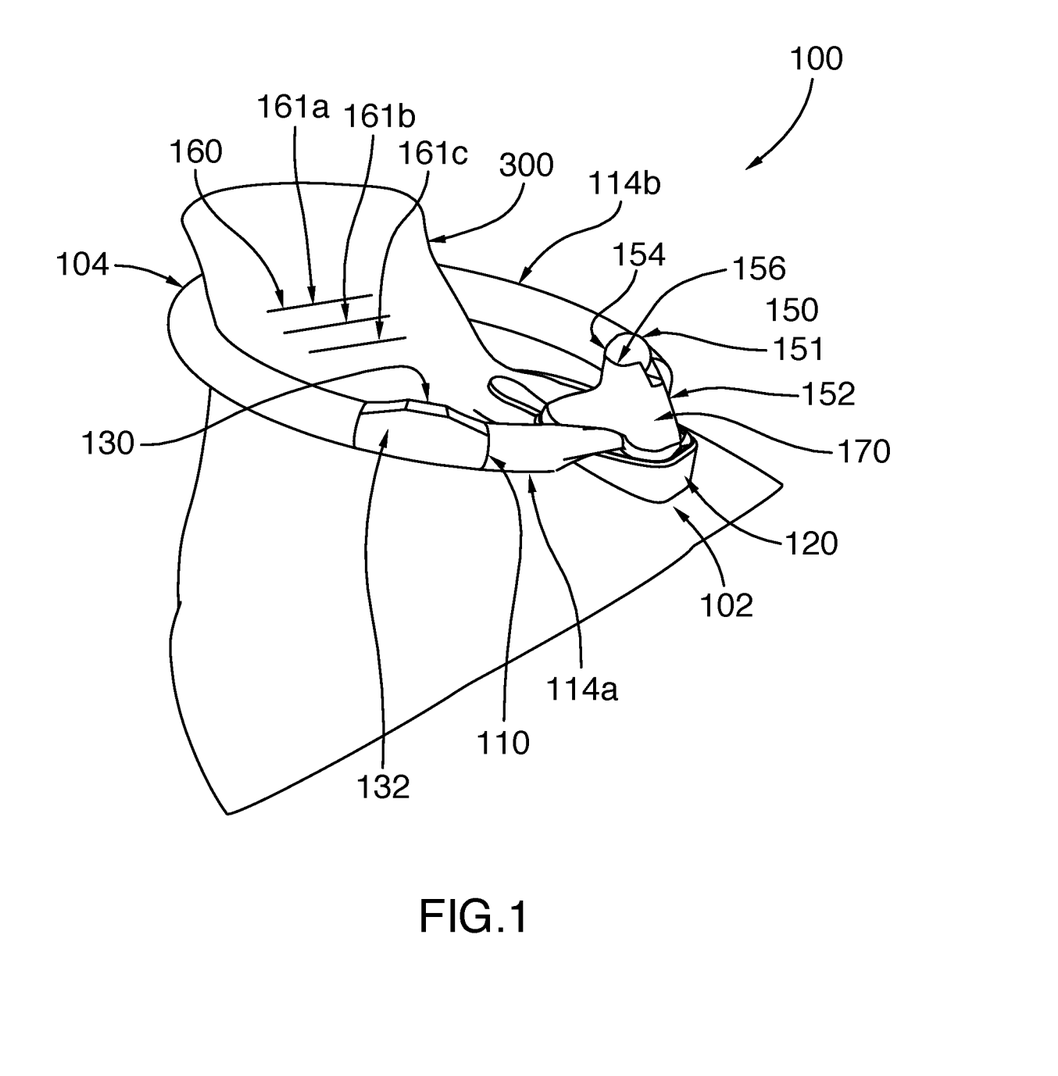
FIG. 1 is a perspective view of a jugular venous pressure measurement device according to one implementation of the present disclosure.
Figure 4:
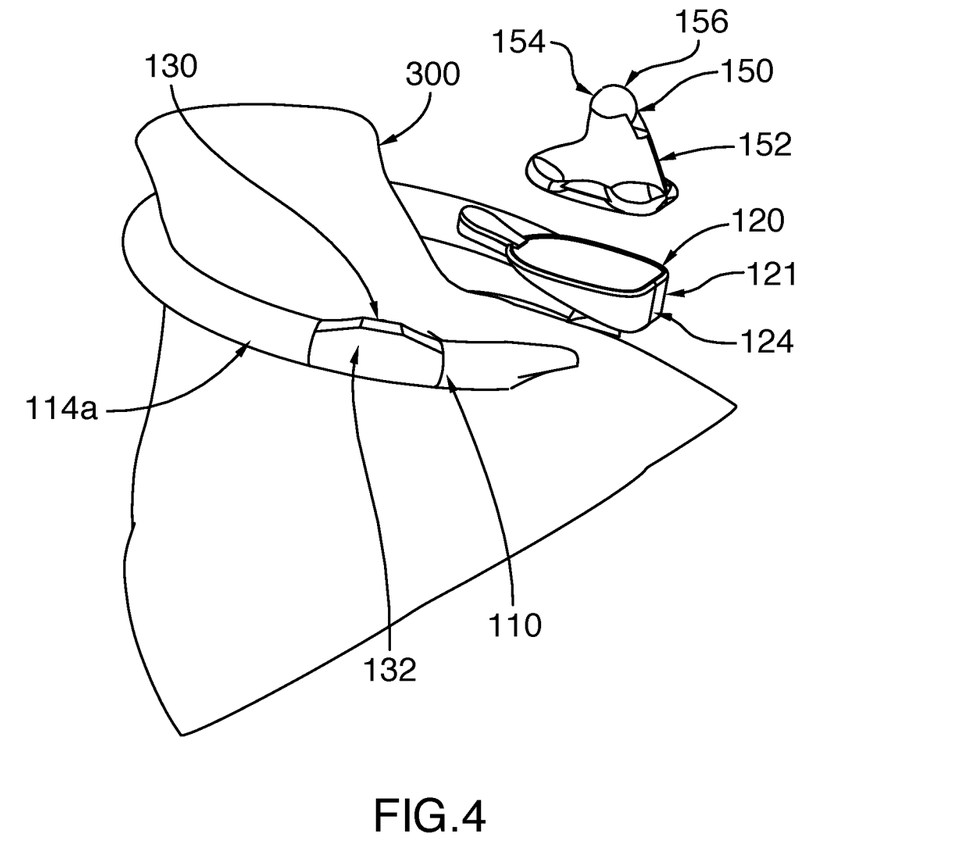
FIG. 4 is a perspective exploded view of the jugular venous pressure measurement device of FIG. 1.

In this implementation, the body 110 of the device 100 is an annular ring in the shape of a torus or 'donut'. The torus shape prevents the device 100 from dropping off the neck of the patient and also provides a large surface area for the device 100 to rest on, stabilising the camera 130 on the chest to generate reproducible and consistent video footage with the region of interest on neck. The torus shape is comprised of two side arms 114a, 114b extending out from the central body 152 and being removably joined in a rear portion 104 of the body 110 proximal to a rear end of the patient's neck 300. The side arms 114a, 114b may be made of plastic or any other material that allows elastic deformation of the side arms 114a, 114b, allowing them to be removably fitted around the patient's neck 300. The side arms 114a, 114b may be joined by any kind of mechanical lock such as a hook and eye fastener, a magnetic lock or any other fastening means deemed appropriate by the skilled addressee. Alternatively, the side arms may be detachable from the light emitter assembly body 152 to allow them to connect around the patient's neck. In an alternative implementation, the side arms 114a, 114b may only partially surround the neck 300 of the patient without being joined at all.

Figure 2:
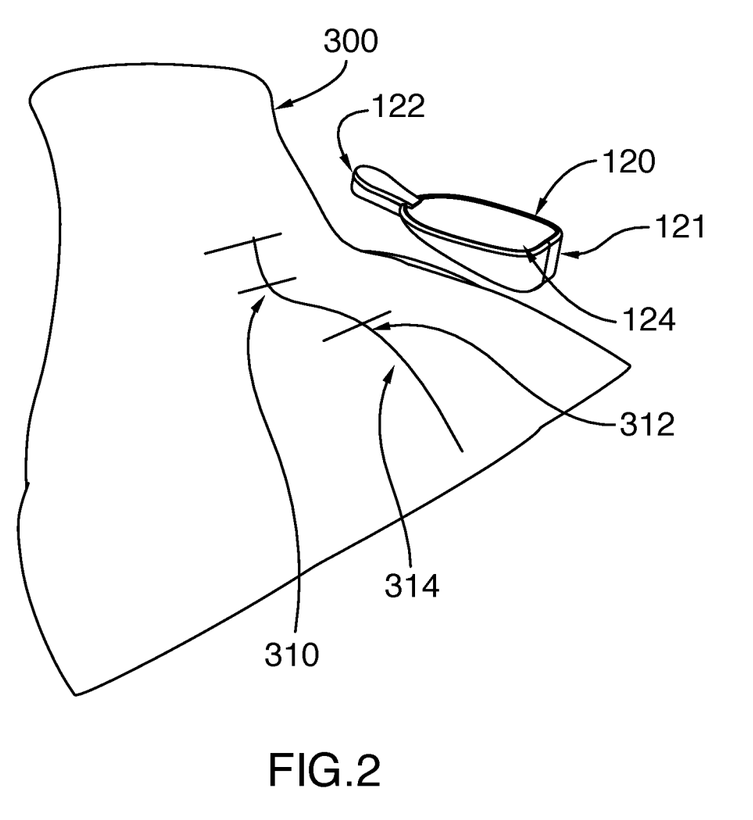
FIG. 2 is a perspective view of the base of the light assembly portion of FIG. 1.

At a front portion 102 of the device body 110, there is a light emitter assembly 150 including a light emitter 154 and central body 152 mounted onto a base 120. The base 120 is a generally round structure sized and shaped to be received on a sternal angle 312 of the patient located between the manubrium 310 and the sternal body 314 (see FIG. 3). The base 120 may additionally comprise a tab 122 extending outwardly from the base 120 towards the neck 300 of the patient, and adapted to largely fit the shape of the manubrium 310 to improve positioning of the light emitter assembly 150 on the sternal angle 312. Other positions for the light emitter assembly 150 may be selected as needed, including the rib spaces or the clavicle. The base 120 has a light emitter assembly receiving portion 124 adapted for receiving a light emitter assembly 150 therein. The tab 122 and the main body 121 of the base 120 together result in a generally tear shaped base 120, though other shapes may be evident to the skilled addressee.

In this implementation, the base 120 is equipped with an orientation sensor (not shown—which may be either of a 3-axis accelerometer or gyroscope) in order to provide information on the orientation of the base 120. The orientation sensor may comprise one or more of a photodetector, a pressure sensor, a microphone, a pulse oximeter, an electrode (such as an electrocardiogram electrode) or other sensor. A pressure sensor may, for example, determine if the device is held against a surface while a photodetector at the bottom of the device can act similarly. The device 100 may be configured to only project a light pattern 160 when this sensor detects correct orientation. In some embodiments, a pulse oximeter may be additionally added to the base 120 to monitor the amount of oxygen carried by the blood. In 30) such embodiments, the base 120 would need to be positioned on the patient's skin (as opposed to over clothing) and the device 100 may additionally be capable of determining heart rate, respiratory rate and oxygen saturation.

Figure 3:
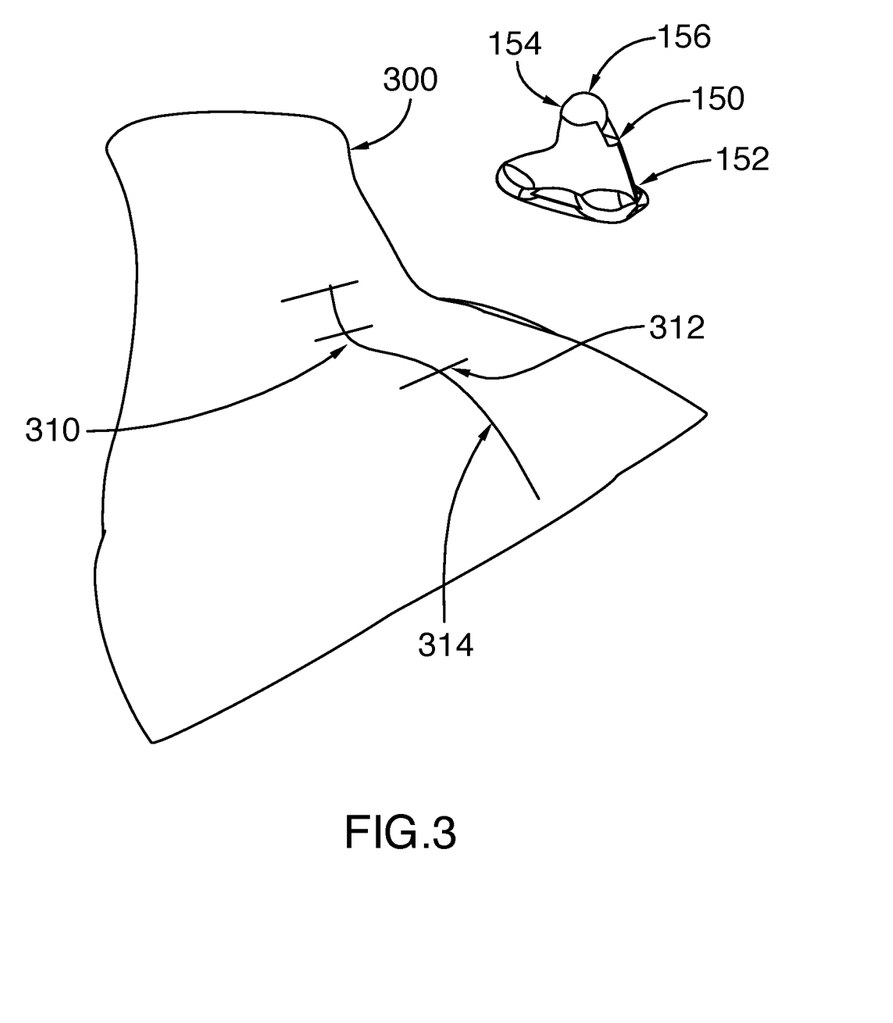
FIG. 3 is a perspective view of the light emitter assembly of FIG. 1.

The central body 152 has a generally longitudinal shape and extends upwardly at a central location of the front portion 102 of the device body 110. In the present implementation, the central body 152 extends upwardly 6 cm. In other implementations, the light body 152 extends upwardly between 2 cm and 20 cm, and in other implementation between 6 cm and 8 cm.

At a top portion 151 of the central body 152, there is installed a gimbal 156. The gimbal 156 is coupled with the light emitter 154 and stabilizes the light emitter 154 to prevent vibrations or other instabilities from distorting the projection of the pattern of light 160. In some implementations, the gimbal 156 only provides stability in a single axis (e.g., the vertical axis) while also allowing rotation, while in other implementations the gimbal 156 is a three-axis gimbal to maintain the absolute position of the light emitter 154 or allow rotation along any of the three axes. In some implementations the gimbal 156 may further include position sensors and actuators to move the light emitter 154 to a specific orientation. The gimbal 156 has a generally spherical shape in the three-axis configuration and a cube shape in the single-axis configuration, though other shapes and configurations will be evident to the skilled addressee.

The gimbal 156 may further include an orientation sensor, such as a single or multi-axis accelerometer. In some implementations, the device may be configured to only project a light pattern 160 when the device 100 is within a predetermined tolerance of the vertical. In some embodiments, the light emitter 154 may only project light when the device 100 is within 2 or within 5 degrees of the vertical.

In this implementation, with the gimbal at 6 cm, the device is calibrated with the patient being at a recumbent angle of 45 degrees. As was discussed above, it is possible that the device may be used by a patient at a different angle than 45 degrees, most likely at angle of between 30 degrees and 60 degrees. A slight error in the height of the JVP will be introduced as the recumbent angle of the patient deviates 45 degrees. The greater the deviation, the greater the error. At 30 degrees or 60 degrees the error is +0.2 cm, which is believed to be acceptable. (In fact, a greater error may also be acceptable in some situations.)

In this implementation, the light emitter 154 transmits a plurality of light sheets. The light pattern 160 formed when the projected light intersects with the neck of the patient) is composed of three lines of light 161a-161c along three horizontal planes offset from one other. In this implementation, a beam of light is passed through a lens to create the plurality of lines of light 161a-161c. When a patient is inclined at an angle of approximately 45° from the vertical, the light emitter 154 is positioned and oriented to be aligned with the horizontal plane. In this configuration, the lines of light 161a-161c are equidistantly spaced apart from one another. In different implementations, the lines of light 161a-161c may be between 2 cm, 3 cm or 4 cm apart from one another. Although a plurality of lines 161a-161c form the light pattern 160 in this implementation, other light patterns are also possible. For example, an additional light beam may be used to project a scale proximate to the pattern of light. Alternatively, the pattern of light may be different from the three lines of light 161a-161c, for example being any shape that has a defining feature (e.g., a grid, an edge, a corner or the like). The device 100 additionally may include a white LED or any other light (not shown) to illuminate the region of interest on the neck 300 of the patient.

On one of the side arms 114a, 114b of the device 100 is installed a camera 130 for recording images of the patient's neck 300, particularly for recording an image of the height of a column of blood in a neck vein (i.e., internal jugular vein) being shown using the pattern of light 160. The camera may be oriented roughly in the same direction as the projected light pattern 160 (possible alignment might differ somewhat to ensure optimal imaging of the neck—depending on the image capture angle of the camera). In other implementations, the device 100 may not have an integrated camera 130 but may instead be used with a camera of another device (e.g., a smartphone that is securely held in a single reproducible position). The camera 130 may be any camera that allows for recording both static imagery as well as videos and with a resolution which permits determination of the height of the column of blood through analysis of the image. In one implementation, the camera 130 starts recording video of the patient's neck prior to or at the same time the pattern is projected and thus is able to capture video of the patient's neck 300 (with the pattern projected thereon) for a period of 5 to 60 seconds. In some implementations the camera 130 captures video of the patient's neck 300 for a period that includes a number of cardiac cycles. In some implementations the camera 130 captures video of the patient's neck 300 for a period including a number of respiratory cycles. The camera 130 may also be coupled to a gimbal (not shown) similar to the gimbal 156 of the light emitter 154 to both allow orientation of the camera 130 along one or all three axes, as well as provide stability to the camera 130 to reduce the possibility of faulty readings. In one implementation, the camera 130 may additionally be adjustable laterally along the side arms 114a, 114b.

In some implementations, the pattern is projected just long enough to provide sufficient frames (images) for processing the images to register the height of the pattern 160 with respect to the base 120 of the device 100 with the video, and to add a computer-generated scale to the side of the neck in the images (so as not to obstruct view of the neck) to facilitate review.

In one implementation, the camera 130 transmits the recorded images using a communication interface (not shown), e.g., Wi-Fi, Bluetooth, etc., to a remote (receiving) device (not shown) for processing. The remote device may be a computer, a smartphone, a tablet, a remote server or any other device which allows reception of data and processing thereof. The remote device may have dedicated software for processing the received images. For example, the remote device may have software allowing a person to visually review the images to determine the jugular venous pressure of the patient (remotely). In such case, the software may additionally overlay a computer-generated scale to facilitate review of the recorded images.

In other implementations, the video may alternatively or additionally be analyzed by artificial intelligence (e.g., a machine learning algorithm) to determine the JVP and/or to adjust treatment. The software may additionally be configured to determine whether a good quality video has been captured, to reformat the video, to perform lossless compression, to perform compression, or perform other image processing operations. The data or images may be configured to be stored on a remote server or on a local storage device (e.g., the local computer or phone), as well being retained on the device 100 itself.

In some implementations, the device may comprise a user interface that, in a non-limiting example, includes a green LED to indicate a successful recording has been completed, and a red LED to indicate that the video has not been recorded.

A battery or series of batteries (not shown) may be provided in the device 100 for powering the light emitter 154, gimbal 156 actuator, the camera 130 and the communication interface to ensure portability of the device 100. There is additionally a switch 170 for turning the device 100 on or off to conserve the battery.

Modifications and improvements to the above-described implementations of the present technology may become apparent to those skilled in the art. The foregoing description is intended to be exemplary rather than limiting. The scope of the present technology is therefore intended to be limited solely by the scope of the appended claims.

The invention claimed is:

1. A device for imaging the neck of a human patient, the device comprising:
 a support structure configured to rest on the patient, the support structure comprising a base, the base comprising a protrusion configured to fit with an anatomical landmark of the patient, such that when the support structure is contacted with the body of the patient and the protrusion is fitted with the anatomical landmark, the support structure rests on the body in a prescribed position and orientation;
 a light emitter assembly supported by the support structure and positioned or positionable to project light onto the neck of the patient proximate to the patient's jugular vein when the support structure rests on the body in the prescribed position and orientation; and
 at least one camera supported by the support structure, the at least one camera being positioned and oriented to capture images of the neck with the light projected thereon.

2. The device of claim 1, wherein the protrusion is configured to fit with the sternal notch.

3. The device of claim 1, wherein the protrusion is configured such that the fit with the anatomical landmark results in pre-determined alignment with one or more of the manubrium, sternum and sternal angle of the patient.

4. The device of claim 1, wherein the support structure is configured to wrap at least partially around a side of the patient's neck or the patient's shoulders.

5. The device of claim 1 wherein the support structure is further configured to wrap around a side of the patient's neck or the patient's shoulders.

6. The device of claim 1 wherein the light emitter assembly is moveably supported via a light-emitter-assembly support gimbal so as to be self-orienting at least with respect to a predetermined plane.

7. The device of claim 1, wherein the at least one camera is moveably supported via a camera support gimbal to allow for positioning of the at least one camera's image sensor.

8. The device of claim 1, further comprising at least one processor, the at least one processor being in electronic communication with:
 the light emitter assembly for controlling the light emitter assembly; and
 the at least one camera for controlling the at least one camera.

9. The device of claim 8, wherein:
 the light emitter assembly is moveably supported to allow for positioning of the light;
 the device further comprises:
  a light-emitter-assembly actuator for moving the light emitter assembly; and
  a light-emitter-assembly sensor configured to detect at least one of a position and an orientation of at least a part of the light emitter assembly; and
 the at least one processor is further in electronic communication with;
  the light-emitter-assembly sensor for receiving information related to the at least one of the position and the orientation of the at least a part of the light emitter assembly; and
  the light-emitter-assembly actuator for controlling the light-emitter-assembly actuator.

10. The device of claim 8, wherein:
 the device further comprises a camera sensor configured to detect at least one of a position and an orientation of the camera; and
 the at least one processor is further in electronic communication with the camera position sensor for receiving information related to the at least one of the position and the orientation of the camera.

11. The device of claim 10, wherein:
 the at least one camera is moveably supported via a camera support gimbal to allow for positioning of the at least one camera's image sensor;
 the device further comprises a camera actuator for moving the at least one camera; and
 the at least one processor is further in electronic communication with the camera actuator for controlling the camera actuator.

12. The device of claim 11, wherein:
 the light emitter assembly is moveably supported, to allow for positioning of the light;
 the device further comprises:
  a light-emitter-assembly actuator for moving the light emitter assembly; and
  a light-emitter-assembly sensor configured to detect at least one of a position and an orientation of at least a part of the light emitter assembly; and
 the at least one processor is further in electronic communication with:
  the light-emitter-assembly sensor for receiving information related to the at least one of the position and the orientation of the least a part of the light emitter assembly; and
  the light-emitter-assembly actuator for controlling the light-emitter-assembly actuator.

13. The device claim 11, further comprising an information storage medium in electronic communication with the processor, the information storage medium containing instructions that, when executed by the at least one processor, cause:
 projection of the light onto the neck of the patient proximate to the patient's jugular vein; and
 capture of images of the patient's neck having the light projected thereupon.

14. The device of claim 13, wherein the information storage medium contains further instructions that, when executed by the at least one processor, cause:
 processing of the captured images to determine the jugular venous pressure of the patient.

15. The device of claim 13, wherein the at least one processor and the information storage medium are positioned within any one of:
 a cavity defined within the support structure;
 at least one of the at least one camera; and
 a housing for the at least one camera and the light emitter assembly.

16. The device of claim 13, further comprising a device sensor, the at least one processor further being in electronic communication with the device sensor for receiving information from the device sensor.

17. The device of claim 16, wherein the device sensor is configured to detect at least one of a position and an orientation of the device.

18. The device of claim 16, wherein the device sensor includes at least one of a pressure sensor, a photodetector, a microphone, a pulse oximeter, electrocardiogram electrodes, a gyroscope and an accelerometer.

19. The device of claim 13 wherein the at least one processor is configured to generate and overlay a height scale on the images captured by the camera, thereby facilitating visual inspection and determination of a jugular venous pressure height.

20. The device of claim 1, wherein at least a portion of the support structure is removably attached for customization of the device to the patient.

21. The device of claim 1, wherein the base is removably attached a remainder of the support structure.

22. The device of claim 1, further comprising an additional light source spaced apart from the light emitter assembly, the additional light source providing lighting on the patent's neck.

23. The device of claim 1 wherein the light emitter assembly is configured such that the light is projected as a light pattern.

24. The device of claim 23 wherein the light pattern is projected such that elements of the projected light pattern have a known height relative to the sternal angle of the patient.

* * * * *